US006926687B2

(12) United States Patent
Shields

(10) Patent No.: US 6,926,687 B2
(45) Date of Patent: Aug. 9, 2005

(54) ANKLE-FOOT ORTHOSIS

(76) Inventor: Daniel J. Shields, 35 Jackson St., Newnan, GA (US) 30263

( * ) Notice: Subject to any disclaimer, the term of this patent is extended or adjusted under 35 U.S.C. 154(b) by 0 days.

(21) Appl. No.: 10/950,854

(22) Filed: Sep. 27, 2004

(65) Prior Publication Data

US 2005/0070833 A1 Mar. 31, 2005

Related U.S. Application Data

(60) Provisional application No. 60/506,558, filed on Sep. 26, 2003.

(51) Int. Cl.[7] ................................................ A61F 5/00
(52) U.S. Cl. .............................. 602/24; 602/27; 602/28; 602/29; 128/882
(58) Field of Search .............................. 602/24, 23, 27, 602/28, 29, 30, 60, 61, 62, 65, 66, 5; 623/27, 28, 29, 47; 128/869, 882; 2/22

(56) References Cited

U.S. PATENT DOCUMENTS

| 4,289,122 | A | * | 9/1981 | Mason et al. | 602/27 |
| 5,088,479 | A | * | 2/1992 | Detoro | 602/27 |
| 5,219,324 | A | * | 6/1993 | Hall | 602/28 |
| 5,370,604 | A | * | 12/1994 | Bernardoni | 602/27 |
| 5,799,659 | A | * | 9/1998 | Stano | 128/882 |
| 5,897,515 | A | * | 4/1999 | Willner et al. | 602/27 |
| 6,409,692 | B1 | * | 6/2002 | Covey | 602/5 |
| 6,676,618 | B2 | * | 1/2004 | Andersen | 128/882 |
| 6,726,645 | B1 | * | 4/2004 | Davis | 602/27 |
| 6,827,696 | B1 | * | 12/2004 | Maguire | 602/27 |
| 6,860,864 | B2 | * | 3/2005 | Meyer | 602/27 |

* cited by examiner

Primary Examiner—Fadi H. Dahbour
(74) Attorney, Agent, or Firm—Needle & Rosenberg, P.C.

(57) ABSTRACT

An ankle-foot orthosis for relief of a patient from orthopedic dysfunctions comprising, in combination, a shoe and a brace assembly. The brace assembly comprises a leg member and a pair of opposed upright members. The leg member is constructed and arranged such that portions of the inner surface of the leg member complementarily conform to portions of the rear and sides of a patient's lower leg. Each upright member of the pair of upright members is connected to the leg member and extends downwardly from the leg member to a distal end. The support brace further comprises means for resiliently connecting a portion of the support brace to the upper portion of the shoe. In use, at least a portion of the distal ends of the upright members is inserted into a portion of the heel portion of the shoe between sides of the shoe and the patient's foot.

36 Claims, 5 Drawing Sheets

US 6,926,687 B2

ANKLE-FOOT ORTHOSIS

This application claims priority to and the benefit of U.S. Provisional Application No. 60/506,558, entitled "ANKLE-FOOT ORTHOSIS," filed on Sep. 26, 2003, which is incorporated in its entirety in this document by reference.

FIELD OF THE INVENTION

This invention relates to an ankle-foot orthosis, and more particularly to a device which is connected to the user's calf and shoe to minimize uncontrolled plantarflexion, inversion and eversion of the foot while walking.

BACKGROUND

Drop foot is characterized by an insufficient control to check plantarflexion, inversion and/or eversion of the foot while walking. Consequentially, a victim suffering from drop foot walks with the toe of an affected foot dragging along the ground. Further, the affected foot may twist inversionally or eversionally. Either or both symptoms provide a sufferer of drop foot with an embarrassing and unsafe gait. Generally, drop foot is incurred by stroke victims, multiple sclerosis patients and/or those suffering from neurological, muscular and/or orthopedic pathological conditions. Victims of any of these pathological conditions can be especially prone to medical complications which may result from a fall caused by tripping due to the drop foot stride.

Drop-foot sufferers can greatly improve their gait and safety by utilizing an ankle-foot orthosis. These devices are designed to mechanically limit the plantarflexional range of motion in the affected foot to something approaching normal. Rehabilitation programs include the use of these devices to assist the patient in developing as near normal gait as possible and to minimize the social impact the pathology imposes on the patient's mobility. Such devices may provide, in addition to controlling runaway plantarflexion, sufficient torsional rigidity to prevent inversion and/or eversion of the foot. The devices may also be comfortable to wear, easy to apply and use, affordable, inconspicuous, fully adjustable to the user's particular physiology, and may be used with a wide range of conventional off-the-shelf footwear styles.

SUMMARY

The ankle-foot orthosis of the present invention provides relief of a patient from orthopedic dysfunctions, such as, for example, drop-foot. In one embodiment, the orthosis comprises a conventional shoe and a brace assembly in combination. The brace assembly includes a support brace and a means for resiliently connecting a portion of the support brace to an upper portion of the shoe.

The support brace includes a leg member and a pair of opposed upright members. In one aspect, the leg member has an inner surface and an opposed outer surface and can be shaped to curve generally concavely laterally between a pair of side edges of the leg member. In another aspect, the leg member can be constructed and arranged such that portions of the inner surface of the leg member complementarily conform to portions of the rear and sides of a patient's lower leg. Each upright member of the pair of upright members is connected to a portion of the leg member proximate a respective side edge of the leg member. Further, each upright member extends downwardly from the leg member to a distal end. In this example, at least a portion of the distal ends of the upright members are inserted into a portion of the heel portion of the shoe between the side portions of the shoe and the patient's foot.

In an alternative embodiment, the support brace includes a heel cup that is sized and shaped to complementarily overlie and surround a portion of the heel of the patient. The heel cup is constructed and arranged to connect to the distal ends of the upright members. In this example, at least a portion of the heel cup is inserted into a portion of the heel portion of the shoe.

DETAILED DESCRIPTION OF THE DRAWINGS

DETAILED DESCRIPTION OF THE INVENTION

Figure 1:
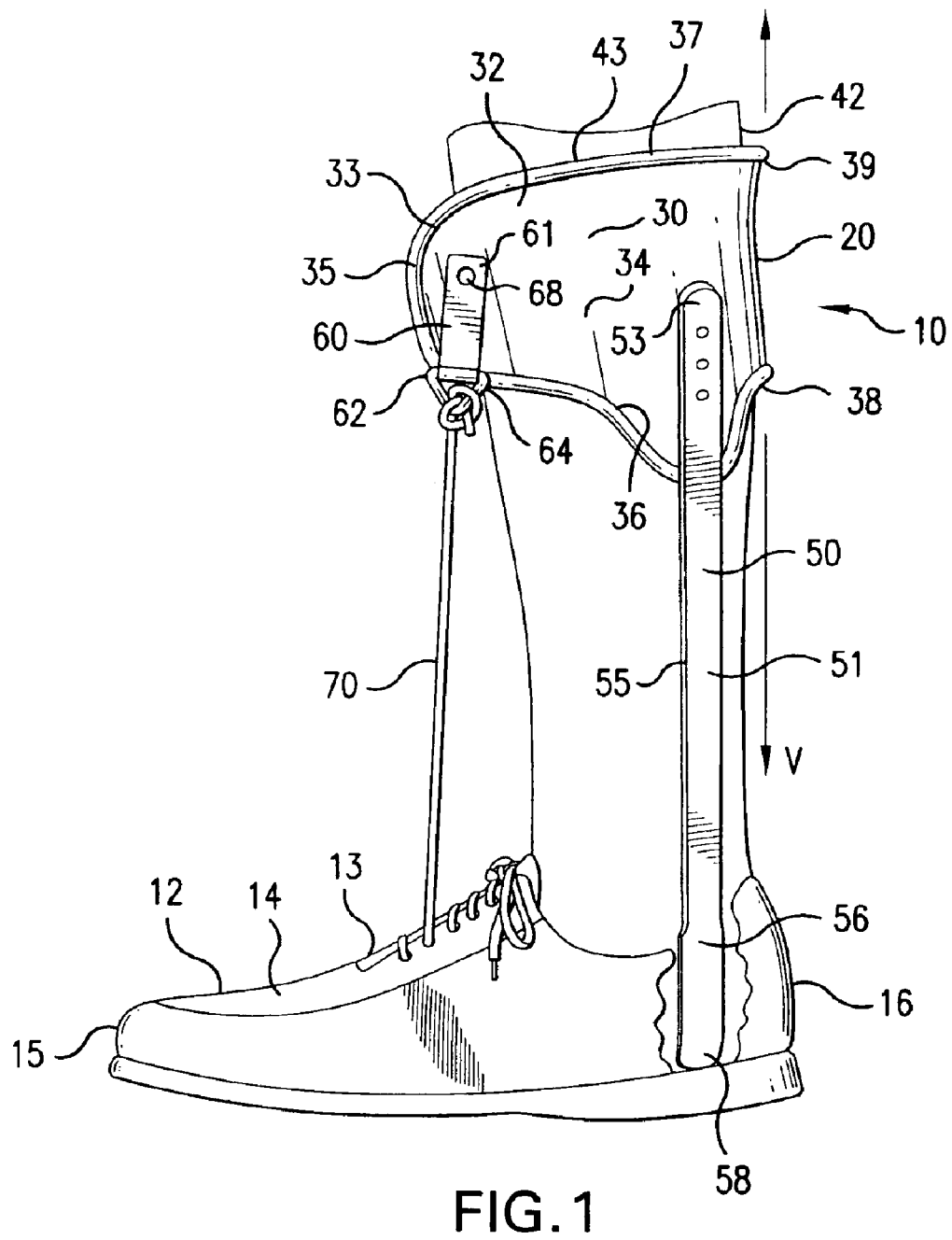
FIG. 1 is a partial broken side elevational view of one embodiment of the orthosis of the present invention as assembled and worn on a left leg or foot.
Figure 2:
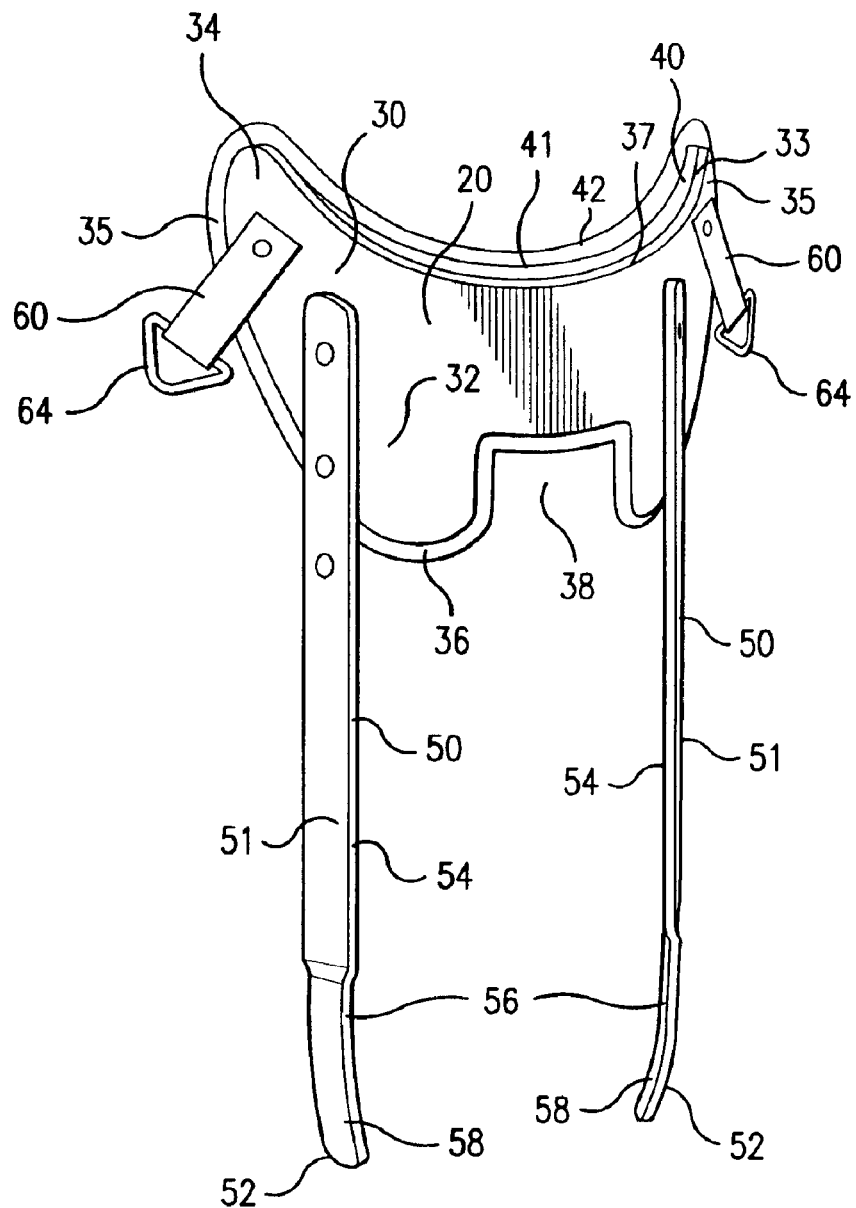
FIG. 2 is a side elevational view showing a support brace of the orthosis of FIG. 1.
Figure 3:
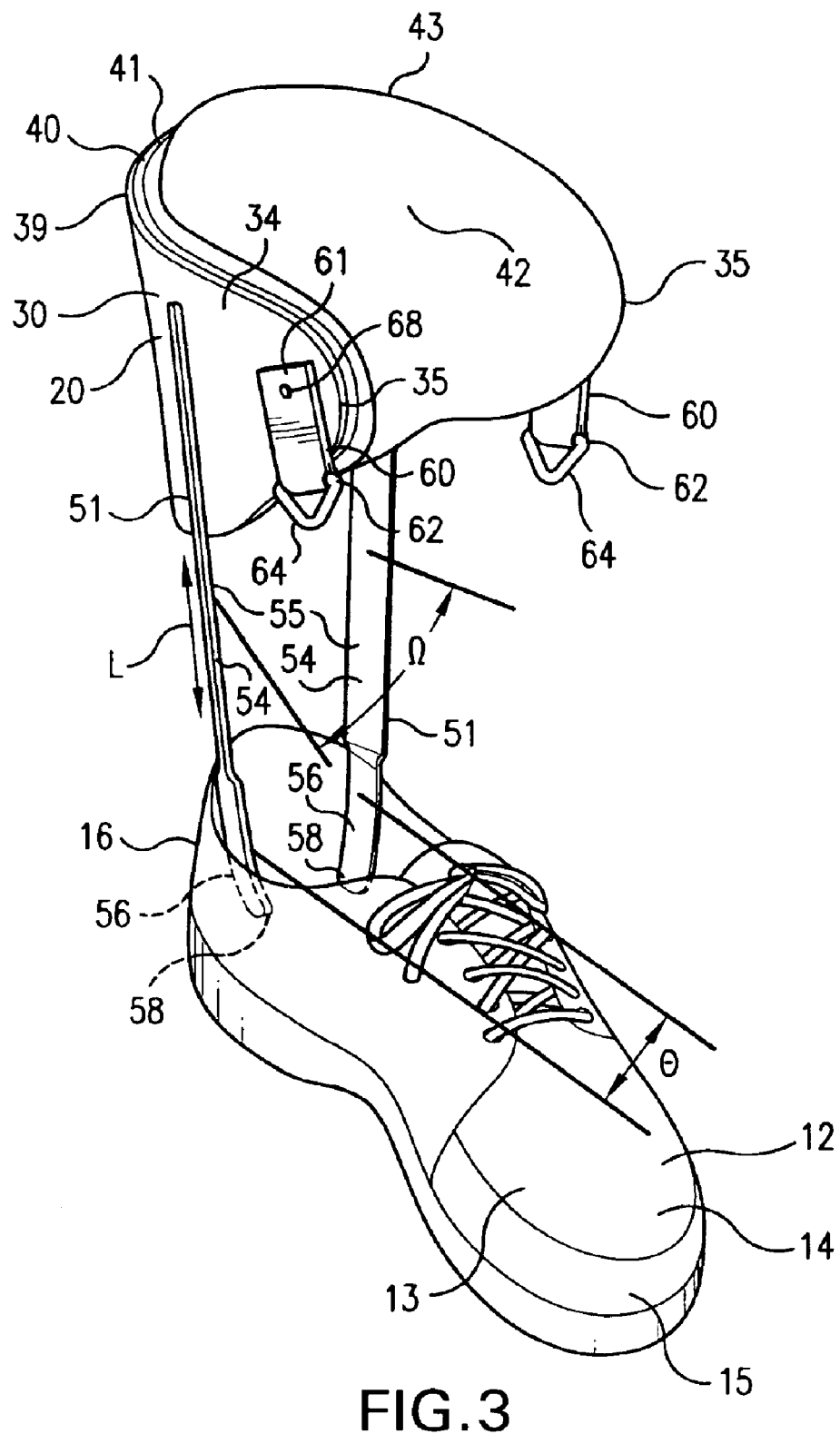
FIG. 3 is a top and front perspective view of the support brace of FIG. 2 disposed within a conventional shoe.
Figure 4:
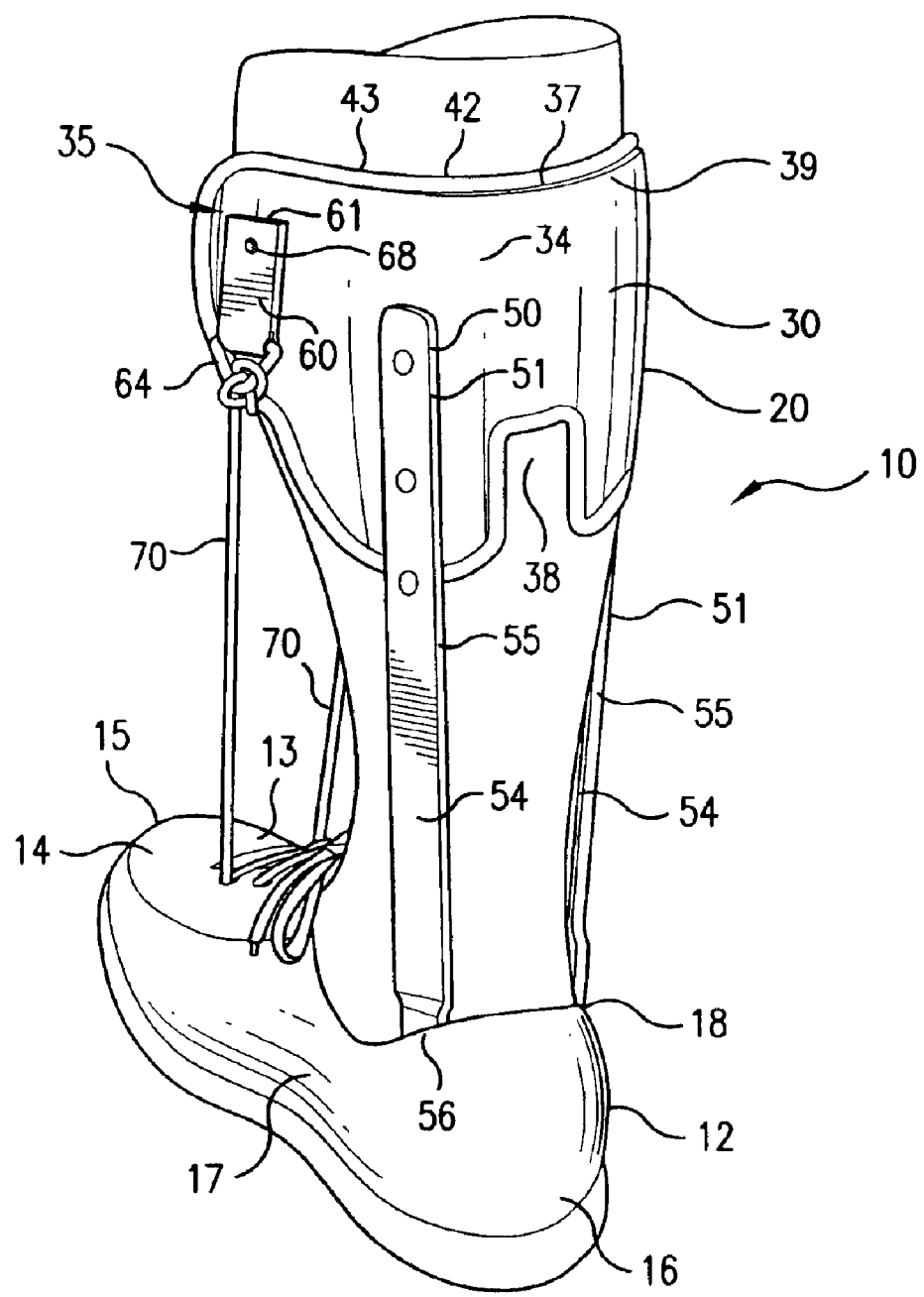
FIG. 4 is a rear three-quarter perspective showing the top, back and left partial views of the support brace of FIG. 2 as assembled and being worn.

The present invention is more particularly described in the following examples that are intended as illustrative only since numerous modifications and variations therein will be apparent to those skilled in the art. Thus, the embodiments of this invention described and illustrated herein are not intended to be exhaustive or to limit the invention to the precise form disclosed. They are chosen to describe or to best explain the principles of the invention and its application and practical use to thereby enable others skilled in the art to best utilize the invention. As used in the specification and in the claims, "a," "an," and "the" can mean one or more, depending upon the context in which it is used. The preferred embodiment is now described with reference to the figures, in which like numbers indicate like parts throughout the figures.

In one embodiment, referring to FIGS. 1–4, the ankle-foot orthosis 10 of the present invention includes a brace assembly 20 and a conventional shoe 12 that work in a cooperative relationship to provide relief from drop-foot, lateral or media-lateral instability and other orthopedic dysfunctions.

The brace assembly comprises a support brace 30 and a means for resiliently connecting a portion of the support brace to an upper portion 13 of the conventional shoe. The shoe 12 has a forward portion 14, which includes a toe 15, a heel portion 16, and a longitudinal vertical plane. The shoe further includes an adjoining first side portion 17 and a second side portion 18 that are bisected by the longitudinal vertical plane. The forward portion, forward part or forepart of the shoe described herein refers to the portion of the shoe that, when the shoe is worn on the foot, is forward of the ankle. The heel portion, back end, back part, rear or rearward part of the shoe refers to the portion of the shoe that, when the shoe is worn of the foot, is behind the ankle portion of the foot and includes the heel portion.

The support brace 30 is constructed and arranged for releasable attachment to a foot drop patient's leg. The support brace 30 includes a leg member 32 and a pair of upright members 50. The leg member has an inner surface 33, an outer surface 34, a pair of spaced side edges 35, and a bottom edge 36. The leg member 32 curves generally concavely laterally between the pair of side edges such that the inner surface 33 of the leg member conforms generally to portions of the rear and sides of the patient's leg proximate their mid or upper calf. In use, the respective side edges 35 of the leg member 30 are disposed to either side of the mid or upper calf, that is, about the posterior aspect of the calf, above and to the rear of the foot. The bottom edge 36 of the leg member defines a slot 38 intermediate the pair of side edges. The slot extends upwardly toward an upper edge 37 of the leg member. The slot 38 is shaped and sized so that bottom edge 36 of the leg member does not bite into or otherwise provide discomfort to the areas of the leg adjacent to and intermediate the mid or upper calf and the heel. Thus, the patient's physical comfort is enhanced by the minimal contact of the leg member as only minimal contact of the posterior aspect of the calf is made by the leg member. The leg member can be formed from conventional metals, composites, polymers, and the like. The leg member can be substantially rigid or it may be at least partially resilient. In one aspect, the leg member is molded from a thermally moldable material.

The patient's physical comfort may be enhanced by securing a first resilient pad 40, such as, for example, a foam pad, to the inner surface 33 of the leg member. The resilient pad 40 may be secured to the inner surface of the leg member by conventional means, such as fasteners, adhesives and the like. In an alternative embodiment, a second removable pad 42 may be releasably secured onto an outer surface 41 of the first resilient pad 40. The second pad may be removable secured to the outer surface of the first resilient pad by conventional fasteners, such as, for example, snap-fit connectors, at least one Velcro-like attachment means, and the like. In one example, the second pad 42 has a peripheral edge 43 that extends beyond the peripheral edge 39 of the leg member so that the discomfort to the patient is minimized. The second pad is preferable constructed of washable materials.

Referring again to the figures, each of the upright members 51 of the pair of upright members 50 is connected to a portion of the leg member intermediate the slot 38 and the respective side edge 35 of the leg member 32. Each upright member 51 extends downwardly from the leg member to a distal end 52. Each of the upright members has a longitudinal axis L and an intermediate portion 55 adjacent the distal portion 58 of the upright member. The upright member may be formed from conventional metals, composites, or polymers, and the like, which are substantially rigid. In use, portions of the distal ends of the each upright member 51 are inserted into opposite side portions of the heel portion of the shoe between the respective side portions of the shoe 12 and the patient's foot. The portions of the distal ends of the upright members are disposed posterior to the medial and lateral condials of the ankle.

The leg member 32 defines an upright axis V extending between the upper edge 37 and bottom edge 36 of the leg member intermediate the respective side edges. In one example, each upright member 51 extends downwardly from the leg member 32 and away from the upright axis as the respective upright member extends from its proximal end 53 towards its distal end 52. Thus, when worn by the patient, each upright member extends substantially along the medial and lateral axis of the patient's leg. Further, the interior faces 54 of the intermediate portion of each upright member 51 that fronts the leg of the patient are positioned at a first angle $\Omega$ with respect to each other. The first angle $\Omega$ is non-parallel. The interior surface 54 of each upright member may be finished smoothly and the edges of each upright member may be rounded so that neither the inside finish nor the edges provide a potential source of discomfort to the patient.

In one embodiment, a portion of the distal end 56 of each upright member is twisted, about and relative to the longitudinal axis of the upright member, toward the other upright member so that the interior faces of the portions of the distal ends 56 are positioned at a second angle $\theta$ that is less than the first angle $\Omega$. The second angle $\theta$ is non-parallel. The distal portion 58 of each upright member may also be curved inwardly toward each other.

Figure 5:
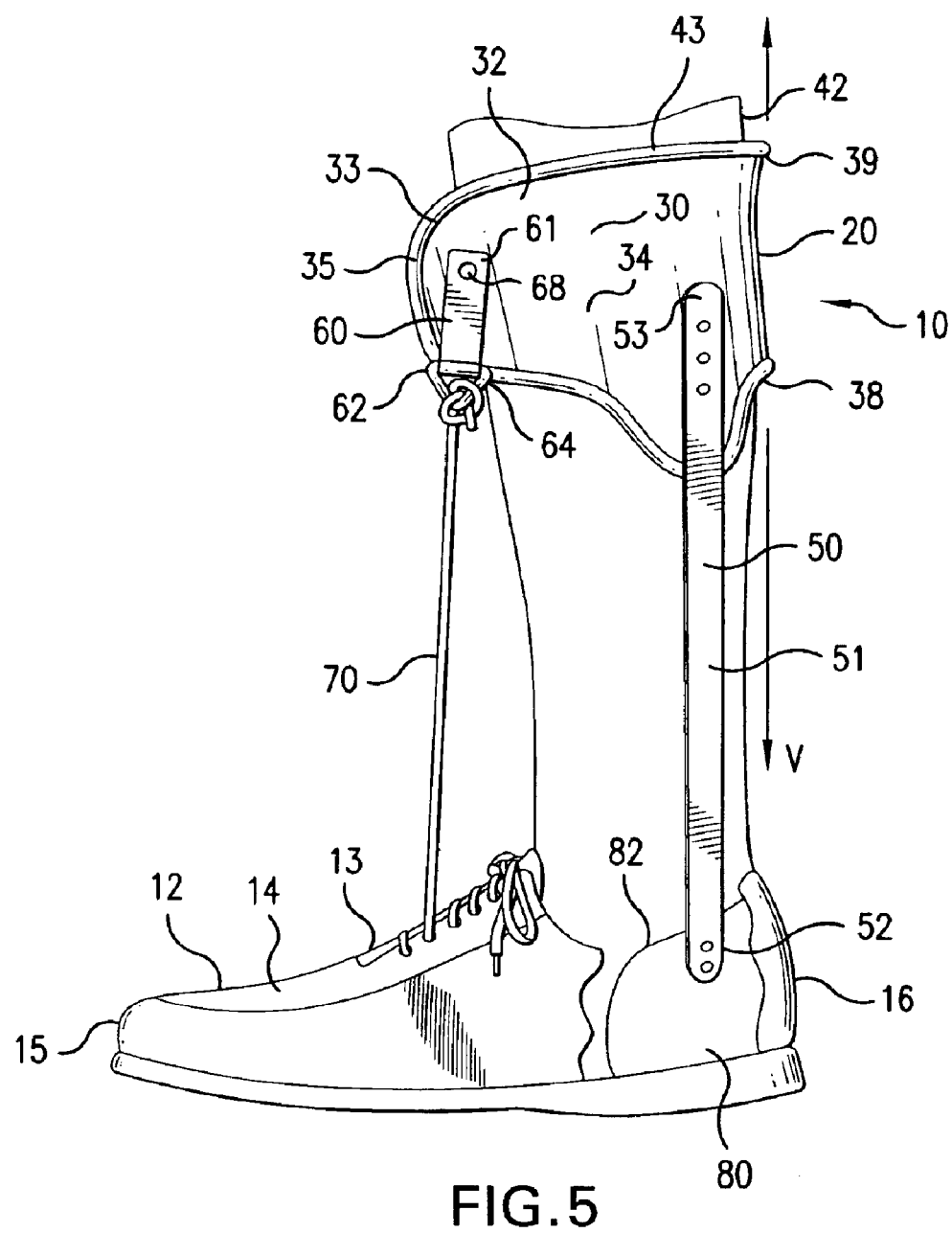
FIG. 5 is a partial broken elevational view of an alternative embodiment of the orthosis of the present invention as assembled and worn on a left leg or foot.

In an alternative embodiment, as shown in FIG. 5, a formed heel cup 80 can be provided that is constructed and arranged to connect to the distal ends of the upright members. The interior portion 82 of the heel cup 80 is formed to concavely laterally partially surround a portion of the heel of the patient. In use, at least a portion of the heel cup is inserted into a portion of the heel portion of the shoe. The heel cup 80 can be formed from conventional metals, composites, polymers, and the like. The heel cup can be substantially rigid or it may be at least partially resilient. In one aspect, the heel cup 80 is molded from a thermally moldable material to at least partially conform to the shape of the patient's heel.

The means for resiliently connecting a portion of the support brace 30 to the upper portion of the shoe 12 comprises a pair of resilient connectors 60. In one aspect, the resilient connection means is connected to a forward portion of the shoe. In one example, each resilient connector is formed from elastic-like material and has a ring 64 connected to its distal end 62 that defines an eyelet 66. The proximal end 61 of one resilient connector is pivotally connected to a portion of the outer surface of the leg member proximate each respective side edge of the leg member by a conventional connector 68 such as, for example, a rivet or a releasable snap-fit button connector. In one example, the proximal end 61 of the resilient connector 60 may be positioned proximate the upper edge 37 of the leg member. The resilient connection means also includes at least one strap 70, which, in one example, may comprise the shoe lace of the conventional shoe.

In one example, in use, the leg member 32 is applied to the posterior of the leg and the distal ends of the upright members 50 are inserted inside the heel portion of the shoe between the shoe and the patient's foot posterior to the medial and lateral condials of the ankle. The at least one strap 70 is extended through the shoe eyelets 19 of the shoe and then up through the two respective eyelets 66 of the rings 64 of the resilient connectors 60. In use, the brace assembly 20 resiliently supports the foot of the patient via the at least one strap 70 attachment to the forward portion of the shoe. In one aspect, the at least one strap is connected to a forward portion of the shoe. In one example, the at least one strap is connected to the shoe eyelets approximately one-third the longitudinal length of the shoe from the toe of the shoe to provide a desired degree of leverage onto the foot.

When worn, the brace assembly 20 of the present invention provides variable dosaflexional tension, which is dependant on how tightly the patient secures the at least one strap 70, to check excessive plantarflexion of the foot when the patient walks. As one will appreciate, the patient can selectively tighten and/or loosen the at least one strap to adjust the selected degree of dosaflexional tension. The resilient connectors 60 of the brace assembly allow for gentle expansion and contraction of the brace assembly that closely approximates the normal mechanics of ankle-foot articulation during walking. Further, the pair of upright members 50 provides a moment arm sufficient to limit inversion or eversion of the foot as it is unweighted with each step. As one will appreciate, the brace assembly 20 is esthetically less obvious to the casual observer as it extends only minimally beyond the anterior aspect of the patient's tibia and may generally be disguised under ordinary trouser legs.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An ankle-foot orthosis for relief of a patient from orthopedic dysfunctions, the orthosis comprising, in combination:
   a) a shoe having an upper portion that includes a forward part and a heel portion, and a longitudinal vertical plane, the shoe further including an adjoining first side portion and a second side portion that are bisected by the longitudinal vertical plane; and
   b) a brace assembly comprising:
      i) a support brace comprising a leg member and a pair of opposed upright members, the leg member having an inner surface and an outer surface, the leg member being shaped to curve generally concavely laterally between a pair of spaced side edges of the leg member and is constructed and arranged such that portions of the inner surface of the leg member complementarily conform to portions of the rear and sides of a patient's lower leg, each upright member of the pair of upright members being connected to a portion of the leg member proximate a respective side edge of the leg member and extending downwardly from the leg member to a distal end; and
      ii) means for resiliently connecting a portion of the support brace to the upper portion of the shoe,
   wherein, in use, at least a portion of the distal end of one upright member of the pair of upright members is inserted into a portion of the heel portion of the shoe between the first side portion and the patient's foot and at least a portion of the distal end of the opposed upright member of the pair of upright members is inserted into a portion of the heel portion of the shoe between the second side portion and the patient's foot.

2. The orthosis of claim 1, wherein the leg member has an upper edge and a spaced bottom edge, and wherein the bottom edge of the leg member defines a slot intermediate the pair of side edges, the slot extending upward toward the upper edge of the leg member and is sized and shaped for complementarily overlying portions of the patient's leg adjacent to and intermediate the patient's calf and heel.

3. The orthosis of claim 2, wherein each of the upright members of the pair of upright members is connected to a portion of the leg member intermediate the slot and the respective side edge of the leg member.

4. The orthosis of claim 1, wherein the leg member further having an upright axis extending between an upper edge and a spaced bottom edge of the leg member, and wherein each upright member has a proximal end, each upright member extending downwardly and away from the upright axis as the respective upright member extends from its proximal end toward its distal end such that, in use, each upright member extends substantially along the medial and lateral axis of the patient's leg.

5. The orthosis of claim 4, wherein each upright member has an interior face, and wherein the interior faces of an intermediate portion of each of the upright members are positioned at a first angle with respect to each other.

6. The orthosis of claim 5, wherein portions of the distal ends of the pair of upright members are constructed and arranged to complementarily overlie portions of the patient's leg posterior to the medial and lateral condials of the patient's leg.

7. The orthosis of claim 5, wherein each upright member has a longitudinal axis, and wherein a portion of the distal end of each upright member is twisted, relative to the longitudinal axis, toward the other opposed upright member so that the interior faces of the portions of the distal ends of the pair of upright members are positioned at a second angle that is less than the first angle.

8. The orthosis of claim 7, wherein the distal portion of each upright member is curved inwardly toward the distal portion of the opposing upright member.

9. The orthosis of claim 1, wherein the means for resiliently connecting a portion of the support brace to the forward portion of the shoe comprises:
   a pair of resilient connectors, each resilient connector having a proximal end and a spaced distal end, each resilient connector having a ring connected to the distal end that defines an eyelet, the proximal end of each resilient connector being pivotally connected to a portion of the outer surface of the leg member proximate each respective side edge of the leg member; and
   at least one strap extending between an upper portion of the forward part of the shoe and the two respective eyelets of the pair of resilient connectors.

10. The orthosis of claim 9, wherein the proximal end of each resilient connector is positioned proximate the upper edge of the leg member.

11. The orthosis of claim 10, wherein the shoe has a longitudinal length extending between a toe of the shoe to a heel of the shoe, and wherein the at least one strap is connected to the upper portion of the shoe a predetermined distance from the toe of the shoe.

12. The orthosis of claim 11, wherein the predetermined distance is approximately one-third of the longitudinal length of the shoe.

13. The orthosis of claim 11, wherein the shoe has at least one shoe eyelet, and wherein the at least one strap extends through at least one of the at least one shoe eyelet.

14. The orthosis of claim 1, wherein the leg member is molded from a thermally moldable material.

15. The orthosis of claim 1, wherein the leg member is substantially rigid.

16. The orthosis of claim 1, wherein the support brace further comprises a first resilient pad mounted to the inner surface of the leg member.

17. The orthosis of claim 16, wherein first resilient pad has an outer surface, and wherein the support brace further comprises a second resilient pad that is removably connected to the outer surface of the first resilient pad.

18. The orthosis of claim 17, wherein leg member has a peripheral edge, and wherein the second pad has a peripheral edge that extends beyond the peripheral edge of the leg member.

19. An ankle-foot orthosis for relief of a patient from orthopedic dysfunctions, the orthosis comprising:
a brace assembly comprising:
a support brace comprising a leg member and a pair of opposed upright members, the leg member having an inner surface and an outer surface, the leg member being shaped to curve generally concavely laterally between a pair of spaced side edges of the leg member and is constructed and arranged such that portions of the inner surface of the leg member complementarily conform to portions of the rear and sides of a patient's lower leg, each upright member of the pair of upright members being connected to a portion of the leg member proximate a respective side edge of the leg member and extending downwardly from the leg member to a distal end; and
means for resiliently connecting a portion of the support brace to an upper portion of a shoe,
wherein, in use, at least a portion of the distal ends of the pair of upright members is inserted into portions of the heel portion of the shoe, wherein each upright member has an interior face and a longitudinal axis, wherein the respective interior faces of an intermediate portion of each of the upright members are positioned at a first angle with respect to each other, and wherein a portion of the distal end of each upright member is twisted, relative to the longitudinal axis, toward the other opposed upright member so that the interior faces of the portions of the distal ends of the pair of upright members are positioned at a second angle that is less than the first angle.

20. The orthosis of claim 19, wherein the leg member has an upper edge and a spaced bottom edge, and wherein the bottom edge of the leg member defines a slot intermediate the pair of side edges, the slot extending upward toward the upper edge of the leg member and is sized and shaped for complementarily overlying portions of the patient's leg adjacent to and intermediate the patient's calf and heel.

21. The orthosis of claim 20, wherein each of the upright members of the pair of upright members is connected to a portion of the leg member intermediate the slot and the respective side edge of the leg member.

22. The orthosis of claim 19, wherein the leg member further having an upright axis extending between an upper edge and a spaced bottom edge of the leg member, and wherein each upright member has a proximal end, each upright member extending downwardly and away from the upright axis as the respective upright member extends from its proximal end toward its distal end such that, in use, each upright member extends substantially along the medial and lateral axis of the patient's leg.

23. The orthosis of claim 22, wherein portions of the distal ends of the pair of upright members are constructed and arranged to complementarily overlie portions of the patient's leg posterior to the medial and lateral condials of the patient's leg.

24. The orthosis of claim 19, wherein the distal portion of each upright member is curved inwardly toward the distal portion of the opposing upright member.

25. An ankle-foot orthosis for relief of a patient from orthopedic dysfunctions, the orthosis comprising, in combination:
a) a shoe having an upper portion that includes a forward part and a heel portion; and
b) a brace assembly comprising:
i) a support brace comprising a leg member and a pair of opposed upright members, the leg member having an inner surface and an outer surface, the leg member being shaped to curve generally concavely laterally between a pair of spaced side edges of the leg member and is constructed and arranged such that portions of the inner surface of the leg member complementarily conform to portions of the rear and sides of a patient's lower leg, each upright member of the pair of upright members being connected to a portion of the leg member proximate a respective side edge of the leg member and extending downwardly from the leg member to a distal end;
ii) means for resiliently connecting a portion of the support brace to the forward portion of the shoe; and
iii) a heel cup sized and shaped to complementarily overlie and surround a portion of the heel of the patient, the heel cup constructed and arranged to connect to the distal ends of the upright members,
wherein, in use, at least a portion of the heel cup is inserted into a portion of the heel portion of the shoe.

26. The orthosis of claim 24, wherein the leg member has an upper edge and a spaced bottom edge, and wherein the bottom edge of the leg member defines a slot intermediate the pair of side edges, the slot extending upward toward the upper edge of the leg member and is sized and shaped for complementarily overlying portions of the patient's leg adjacent to and intermediate the patient's calf and heel.

27. The orthosis of claim 24, wherein each of the upright members of the pair of upright members is connected to a portion of the leg member intermediate the slot and the respective side edge of the leg member.

28. The orthosis of claim 24, wherein the leg member further having an upright axis extending between an upper edge and a spaced bottom edge of the leg member, and wherein each upright member has a proximal end, each upright member extending downwardly and away from the upright axis as the respective upright member extends from its proximal end toward its distal end such that, in use, each upright member extends substantially along the medial and lateral axis of the patient's leg.

29. The orthosis of claim 28, wherein each upright member has an interior face, and wherein the respective interior faces of an intermediate portion of each upright member is positioned at a first angle with respect to each other.

30. The orthosis of claim 24, wherein the leg member is molded from a thermally moldable material.

31. The orthosis of claim 30, wherein the leg member is substantially rigid.

32. The orthosis of claim 24, wherein the heel cup is molded from a thermally moldable material.

33. The orthosis of claim 32, wherein the heel cup is substantially rigid.

34. The orthosis of claim 24, wherein the support brace further comprises a first resilient pad mounted to the inner surface of the leg member.

35. The orthosis of claim 34, wherein first resilient pad has an outer surface, and wherein the support brace further comprises a second resilient pad that is removably connected to the outer surface of the first resilient pad.

36. The orthosis of claim 35, wherein leg member has a peripheral edge, and wherein the second pad has a peripheral edge that extends beyond the peripheral edge of the leg member.

* * * * *